(12) United States Patent
Kuhn et al.

(10) Patent No.: US 8,551,921 B2
(45) Date of Patent: Oct. 8, 2013

(54) METHOD FOR DETERMINING THE TOXICITY OF AN ENVIRONMENTAL OR CHEMICAL SAMPLE

(75) Inventors: Inger Kuhn, Saltsjo-Boo (SE); Patricia Colque-Navarro, Jarfalla (SE); Jenny Gabrielson, Skarholmen (SE); Aina Iversen, Stockholm (SE); John Douglas McKenzie, Oban (GB); Mark Christopher Hart, Oban (GB)

(73) Assignee: Phplate Stockholm AB, Stockholm (SE)

( * ) Notice: Subject to any disclaimer, the term of this patent is extended or adjusted under 35 U.S.C. 154(b) by 615 days.

(21) Appl. No.: 12/028,926

(22) Filed: Feb. 11, 2008

(65) Prior Publication Data
US 2008/0200346 A1    Aug. 21, 2008

Related U.S. Application Data

(62) Division of application No. 10/296,468, filed as application No. PCT/SE01/01169 on May 23, 2001, now abandoned.

(60) Provisional application No. 60/206,779, filed on May 24, 2000.

(30) Foreign Application Priority Data

May 24, 2000    (SE) ...................................... 0001936

(51) Int. Cl.
*C40B 30/06*    (2006.01)
*G01N 33/53*    (2006.01)

(52) U.S. Cl.
USPC ...................... 506/10; 506/7; 435/7.2; 435/4

(58) Field of Classification Search
USPC ............................................ 506/10, 7, 7.2, 4
See application file for complete search history.

(56) References Cited

U.S. PATENT DOCUMENTS

| | | | |
|---|---|---|---|
| 5,372,933 A | 12/1994 | Zamarron et al. | |
| 5,698,398 A | 12/1997 | Shassere et al. | |
| 5,731,163 A | 3/1998 | Vandyk et al. | |
| 6,335,170 B1 * | 1/2002 | Orntoft ............................ | 435/6 |
| 6,479,258 B1 | 11/2002 | Short | |
| 6,716,582 B2 * | 4/2004 | Gonye et al. ...................... | 435/6 |
| 2004/0213771 A1 * | 10/2004 | Sluder et al. ................ | 424/94.1 |

FOREIGN PATENT DOCUMENTS

WO    WO 95/11989    5/1995

OTHER PUBLICATIONS

Pau et al.,. Chem. (1986) 32/6, pp. 987-991.*
Mosmann et al, Jrnl. of Immunological Methods, 65, 1983, 55-63.*
Shelly et al; Clin. Chem. (1983) 29/2, pp. 290-296.*
WPI/Derwent's abstract, Accession No. 2000-389001 week 0034. Abstract of DK, 9900716 (Foss Electric As N) May 21, 1999.

* cited by examiner

*Primary Examiner* — Teresa D. Wessendorf
(74) *Attorney, Agent, or Firm* — Young & Thompson

(57) ABSTRACT

An indicator device, and a biological test method, for determining the toxic fingerprint and degree of toxicity, comprising at least 3, preferably at least 11, different microorganisms freeze-dried on an inert support material, wherein the microorganisms are being selected to form a high diversity of microorganisms, on the support material, with regards to the taxonomical tree and high diversity regarding responses to toxic chemicals. Further, a kit and a process for producing the indicator device is also disclosed.

10 Claims, 4 Drawing Sheets

METHOD FOR DETERMINING THE TOXICITY OF AN ENVIRONMENTAL OR CHEMICAL SAMPLE

The present invention relates to a biological test method for measuring toxicity in vitro, more specific a rapid assay for creating "toxic fingerprints" of chemical compounds or mixtures of compounds. The present invention also provides an indicator device, comprising at least 3, preferably at least 11, different microorganisms immobilized on an inert support material, wherein the microorganisms are being selected to form a high diversity of microorganisms, on said support material, with regards to the taxonomical tree and high diversity regarding responses to toxic chemicals. Further, a kit and a process for producing the indicator device is also disclosed.

BACKGROUND OF THE INVENTION

There are certain microbiological systems known for measuring toxicity. They all involve one single microorganism. Some of them are given in table 1 below.

TABLE 1

Various microbiological systems used for measuring toxicity

| Assay name | Organism/Compound | Type | Microplate assay |
|---|---|---|---|
| Cryoalgotox | Selenastrum capricornutum | algae | x |
|  |  | algae | membrane filter |
|  | E. coli | bacteria |  |
| Microtox | Photobacterium phosphoreum | bacteria | x |
| MetPLATE |  |  | x |
| EROD | etoxy-resorufin-O-deethylase | enzyme | x |
| ECHA | dehydrogenase | enzyme |  |
| MetPAD |  | enzymes |  |
|  | Ps.fluorescence | bacteria |  |
| SOSMA |  |  | x |
| SOS-chromotest | E. coli | bacteria | x |
| SOS lux test | E. coli | bacteria |  |
| Ames test | S. typhimurium | bacteria |  |
| micronucleus | Pleurodeks | amphibian |  |
|  | Caenorhabditis elegans | nematode |  |
| Spirotox | Spirostomum ambiguum | protozoo | x |
|  | Daphnia magna | crustacea |  |
| Toxi-Chromotest | E. coli | bacteria |  |
|  | Artemia salina | crustacea | x |
| CALUX |  | Enzyme |  |
| Polytox |  | bacteria |  |
| VITOTOX | Salmonella typhimurium | bacteria |  |
| METIER | Chironomus riparius |  |  |
| TOXKIT | dormant larvae | Aquatic invertebrate |  |

However these above systems have drawbacks, such as that some has a need for a long sample preparation time and have a high price. Further they may not be read visually which applies for Microtox above. Thus there is in certain of the above systems a need for high cost reading equipment. Time for training of staff would also be considerably longer for some of the systems above.

Biochemical fingerprinting of bacteria is a technique that is used for typing bacterial strains, either to the species level, or for typing below the species level. The unknown bacteria are cultivated in the presence of several different standard chemical compounds, and the ability of the bacteria to metabolise the compounds is measured (the biochemical fingerprint). The results are obtained as a set of quantitative data, and identification of the bacterial strain can be performed by comparing the data to biochemical fingerprints stored in a database that has previously been made using known bacteria. The identification of a bacterial strain to the species level will provide valuable information on the bacteria regarding e.g. pathogenic properties. This method however may not be used for determining toxic effects of unknown chemical compounds.

SUMMARY OF THE INVENTION

The present invention solves the above problem by providing a microbiological test method which solves the above problems i.e. providing a quick and inexpensive test method. Further the method according to the present invention is a reverse biochemical fingerprinting procedure. The chemical compounds with unknown toxic effects are cultivated together with several different standard microbial strains, and the ability of the chemical compounds to inhibit the microorganisms is measured. The results are obtained as a set of quantitative data which may form the basis for a pattern (a toxic fingerprint), and estimation of the biological effects of the compounds can be obtained by comparing the data to patterns (toxic fingerprints) stored in a database that has previously been made using standard chemical compounds with known biological effects. This will provide valuable information on the tested chemical regarding the biological effects it may expose, without the need for testing it on higher organisms.

The present invention provides an indicator device for determining toxicity, in the form of one or more toxic fingerprints, of chemical compounds on microorganisms, comprising at least 3, preferably at least 11, different microorganisms in at least 4 repetitive sets, freeze-dried on an inert support material, wherein the microorganisms are being selected to form a high (taxonomic) diversity of microorganisms, on said support material, with regards to the taxonomical tree and high diversity regarding responses to toxic chemicals. Furthermore a kit and a process for producing the indicator device are also disclosed as well as use of the device and a method for measuring toxicity.

DETAILED DESCRIPTION OF INVENTION

The expression "chemical compound" is meant to embrace in the present description any chemical or mixture of chemicals which may act in a toxic way to animals or other organisms. This chemical compound may also be one hitherto not known compound.

The expression "support material" is meant to embrace in the present description a solid surface such as a membrane filter or microplate which the microorganisms are immobilized on. Preferably the support material is a microplate (ELISA-plate) with 96 wells, or a plate with 384 wells, most preferred 96 wells. Another thinkable microplate for use in the present invention is a microplate with 1536 wells.

The expression "growth medium" is meant to embrace in the present description a medium with which you may obtain good microbial growth. This may only contain a carbon source, nitrogen source and trace elements. A preferred medium may be normal nutrient broth (DIFCO).

The expression "indicator" is meant to embrace in the present description an indicator compound that changes colour on pH-changes, e.g bromothymol blue, or that changes colour due to the microbial growth, e.g. a tetrazolium salt, especially Tetrazolium red (2,3,5-triphenyltetrazoliumchloride) or resazurin. Tetrazolium salts enables measurement of microbial growth and also viability. Upon reduction, the water-soluble colorless tetrazolium compound form uncharged, brightly colored formazans that can be measured visually or by a fluorimeter or a spectrophotometer. MTT 3-(4,5-Dimetylthiazol-2-yl)-2,5-diphenyltetrazolium bromide forms a purple formazan and may be suitable for measuring cell growth and for toxicity testing. An assay medium may comprise growth medium (nutrient broth, NB) and an indicator. An example is an assay medium of 1 L comprising 0,1 g tetrazolium salt, 10 g NaCl and 8 g nutrient broth. Tetrazolium red (2,3,5-triphenyltetrazoliumchloride) precipitates when being autoclaved with nutrient broth, thus either NB and the indicator may preferably be autoclaved as separate solutions or the solution may be sterile filtered. Other examples of tetrazolium salts are TZR, XTT and WST-1. The indicator may be fluorescing. The colour (or fluorescence) may preferably by read visually or by a detection apparatus.

The microorganisms are being selected to form a high taxonomic diversity of microorganisms, on said support material and high diversity regarding responses to toxic chemicals. Further the microorganisms may preferably be non-pathogen, stable and easily lyophilizable on to support materials. Additionally the microorganisms may preferably be easily grown on support material, most preferred in wells of flat-bottomed 96-well microplates. The microorganisms may preferably be sensitive to toxic substances and be able to be grown on commonly used media. Microorganisms may preferably be selected from culture collections or the environment, preferably a marine environment. An example of a set of bacteria for use in a 96-well microplate, i.e. an indicator device according to the present invention, comprises three or more (including all) of the following bacteria: JG1, JG2, JG3, JG4, β-*proteobacterium* A22 (Kalmar 200), *Aeromonas hydriphila* HG3 (RV 5.1), *E. coli* MZ 480, ObanF, *Saccharomyces cerivisiae* (baker's yeast) and *Staphylococcus epidermis* (Karin 12).

The indicator device of the present invention is preferably encapsulated in an air-tight package, most preferred a sealed plastic package, an aluminium package or a combination thereof.

A further preferred embodiment of the present invention is a kit for determining toxicity comprising an indicator device as above, growth medium, with optionally an indicator, and instructions for performing the determination. The kit may be used in any toxicity evaluation, e.g. in pharmaceutical, chemical, marine, agricultural or clinical applications.

A further preferred embodiment of the present invention is a process for the production of an indicator device above comprising the following steps:
a) suspending the microorganisms in a lyophilizing medium containing chemicals that stabilize the microorganisms as well as make the lyophilized microorganisms attach to the support material
b) dispensing microbial suspensions on the support material, preferably into wells of a microplate; and
c) lyophilising of micro-organism on the support material, preferably a microplate.

The process for the production of an indicator device above may preferably be performed in step b) by lyophilisation in a lyophilisation media comprising dextran, glucose and phosphate buffer, preferably comprising about 2% dextran, about 7.5% glucose and about 0.3M phosphate buffer. In general it may be enough that 10% of the microorganisms are viable and may participate in the determination method according to the present invention.

A further preferred embodiment of the present invention is a process for the production of an encapsulated indicator device above comprising the following steps:
a) packing an above indicator device, preferably in the form of a microplate, in an air-tight plastic and/or aluminium bag together with optionally silica gel; and
b) sealing the bag.

The present invention also provides use of an indicator device above for measuring toxicity of chemical compounds (e.g. pollutants) and/or creating toxic fingerprints of chemical compounds by exposing the microbial strains to one or more concentrations of the chemical compound.

A further preferred embodiment of the present invention is a method for identifying the toxic effect of unknown compounds using the toxic fingerprints obtained from the indicator device according to the present invention; and by comparing them to a database.

A further preferred embodiment of the present invention is a method for measuring toxicity of chemical compounds comprising the following steps:
a) adding growth medium, indicator and chemical compound to be evaluated to an indicator device according to the present invention as outlined above;
b) incubating the indicator device; and
c) reading the pattern generated on the indicator device.
Further, said method preferably comprises a step:
d) transforming the pattern to a set of quantitative data indicating the amount of inhibition on each microbial strain (the data set here is named the "toxic fingerprint").

The method may preferably be such that step c) is performed by a reading apparatus which in turn is connected to a computer for recording the pattern. The readings may be performed either several times to produce kinetic patterns, or only once to form end-point results. The toxic fingerprint of the chemical compound obtained in step d) is then either used directly to estimate the toxicity of the chemical compound, or is then compared to an already in the computer stored database containing earlier produced toxic fingerprints of standard chemical compounds. The standard chemical compounds in the database are selected among compounds of which already extensive toxicological data are available, e.g. from animal testing. The comparisons result in similarity coefficients (a correlation) indicating to which standard chemical compounds the toxic fingerprint of the tested compound give the best match. The result may thus give an indication on which toxic effects the unknown compound may exhibit, without the need for other extensive toxicological testing, including animal testing. The similarity coefficients may further be processed by using suitable mathematical pattern recognition methods, and all results are printed on a printer or shown on a monitor.

According to yet another preferred embodiment of the present invention there is provided a computer program stored on a data carrier for performing the above method according to the present invention.

The invention together with the software can be used both to detect the toxic responses of individual compounds and, possibly, to determine the extent of toxicological risk of a complex mixture on the basis of its similarity of response to a model compound of known toxicity and risk may be used to obtain such comparisons. To be able to make any risk evaluation based on the results from using the present invention, a product, e.g. a floppy disc, may also include a database showing responses towards known compounds with known biological and ecological effects. The total assay may thus consist of the indicator device of the present invention, complete with a suitable microplate reading device for use in connection to the indicator device (e.g. a microplate spectrophotometer, a hand or flatbed scanner or a CCD cameras), and a CD or a floppy disk with analytical software and a data base consisting of toxic fingerprints of standard chemical compounds (optionally together with a computer program stored on a data carrier for performing the above method according to the present invention).

The present invention thus provides user-friendly kits for assessment of toxicity, based on multiple organisms and using automated readings and data treatment. Such kits may contain at least 3, or preferably 11-23 organisms in microplates, and they yield a broad range of responses towards added chemicals. Further the support material, preferably microplates, according to the present invention may have at least 4, 5, 6, 7, 8, 9 or 10 sets of the used microorganisms. The objective of the present invention has been to develop novel, user-friendly microbial assay systems suitable for commercial development that can be used for the detection, monitoring and experimental risk evaluation of pollutants and other chemical substances. The system is based on measurements on the effects of potential hazardous agents on a large set of single microorganisms belonging to a diverse range of genera and species The method above of the present invention, a microbial assay for toxicity (risk) assessment, may comprise either 96 well microplates with at least 11 different microbial strains, example of layout shown in FIG. 1, or of 384 well cliniplates with at least 15 (or 22) different sets of microbial strains, examples of layout as in FIG. 2. The total response in the assay would thus consist of a number of breakpoint values, as exemplified in FIG. 1, or of a number of kinetical values. Each 96 well unit may be used to assay one toxic sample at 7 different concentrations, and the 384 well unit may be used for 2 assays at 7 concentrations.

We will now describe the present invention by using figures and examples but they are only for purposes of illustration and shall not in any way limit the scope of the appended set of claims.

FIGURES AND TABLES

Figure 1:
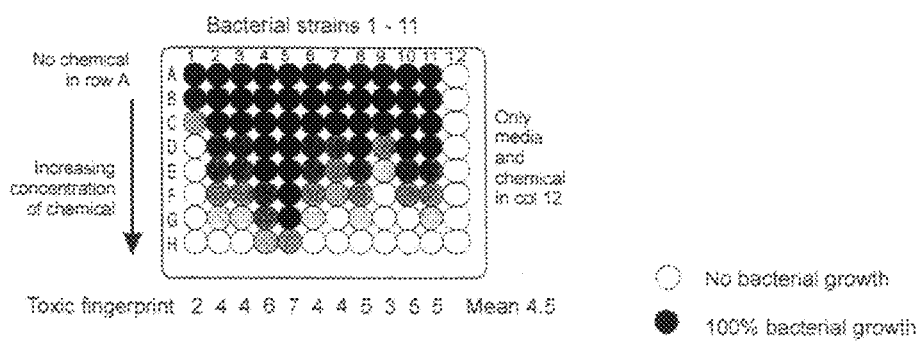
FIG. 1 shows a 96 well version of a MARA plate.
Figure 2:
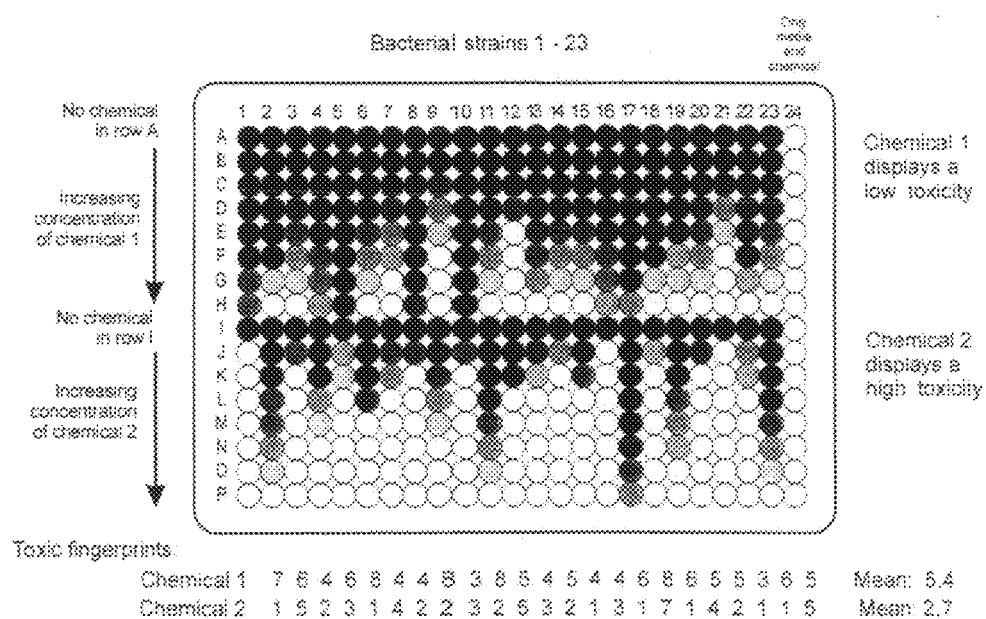
FIG. 2 shows a 384 well version of a MARA plate.
Figure 5:
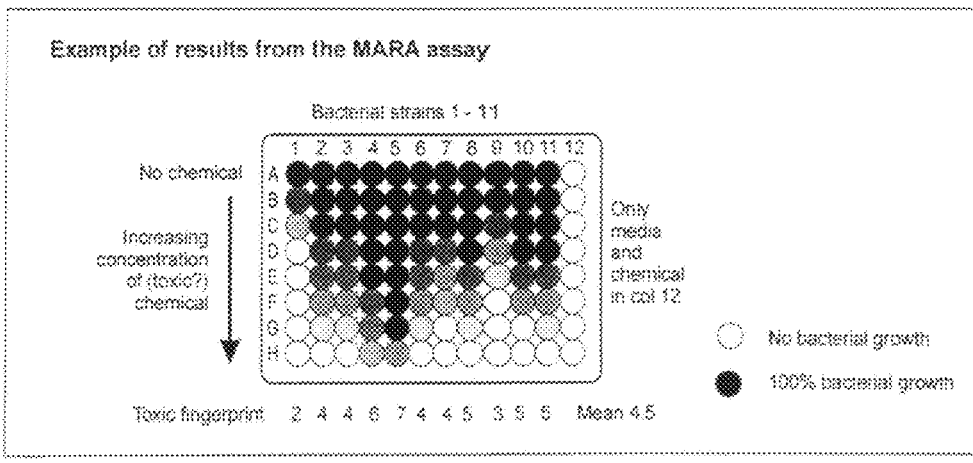
FIG. 5 shows an example of the results you would obtain with the MARA assay.

FIGS. 1 and 2 the indicator device of the present invention (in the figures and tables named the MARA plate—a Microbial Assay for Risk Assessment), comprising 96 well microplates with at least 11 different microbial strains (FIG. 1), or with 384 well cliniplates below with at least 22 sets of microbial strains (FIG. 2). The total response in the assay would thus consist of a number of breakpoint values, as exemplified in FIG. 1 In the 96-well plate, there are 11 microbial strains in columns 1-11 (FIGS. 1, 2) Column 12 has only media and chemical compound, thus this is used as negative control (FIGS. 1, 2). The chemical compound to be assayed is applied using decreasing concentration of chemical in row B-H (FIGS. 1, 2). No chemical compound in row A. The toxic fingerprints can be seen below in the figure. The 384 well microplate allows for two chemicals to be detected at the same time (FIG. 2). There are 23 different microbial strains in columns 1-23. Column 24 is a standard with only media and chemical. Rows B to H as well as J to P has a decreasing concentration of compound 1 and compound 2, respectively (FIG. 2 ). Rows A and I has no chemical. As can be seen chemical 1 displays a low toxicity and chemical 2 displays a high toxicity (FIG. 2). The toxic fingerprints are given below in the FIG. 5.

Figure 3:
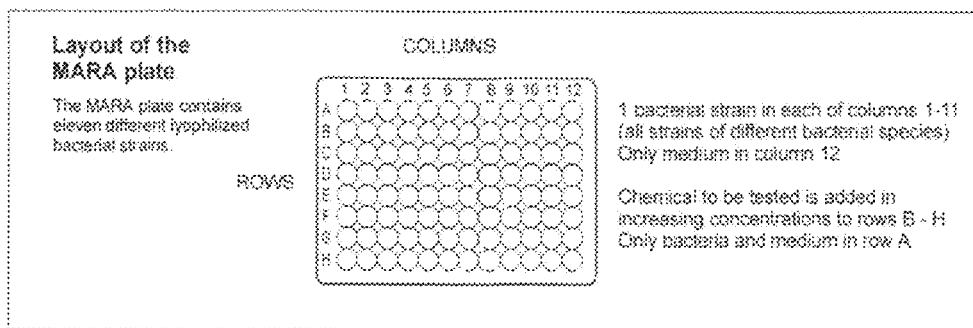
FIG. 3 shows a layout of a MARA plate.
Figure 4:
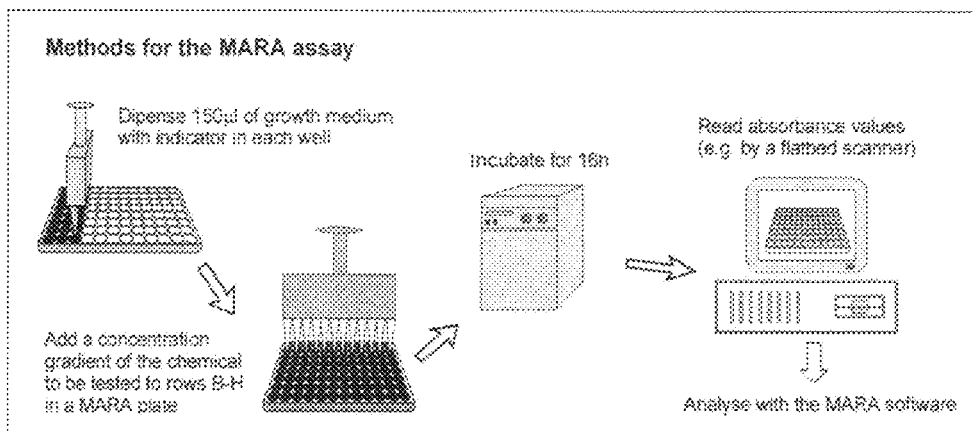
FIG. 4 shows a method of the MARA assay.

FIGS. 2, 3 and 4 show a layout of the indicator device, the principles for handling the indicator device and an example of results from the method according to the present invention. The MARA plate contains eleven different lyophilised bacterial strains. 1 bacterial strain in each column 1-11 (all strains of different bacterial species). Only medium in column 12. Chemical to be tested is added in increasing concentrations to rows B-H. Only bacteria and medium in row A.

Steps of the methods of the assay (FIG. 4):
  dispense 150 µl of growth medium with indicator in each well
  add a concentration gradient of the chemical to be tested to rows B-H in a MARA plate (i.e. an indicator device according to the present invention)
  incubate for 16 h
  read absorbance values; and
  analyse with software.

Figure 6:
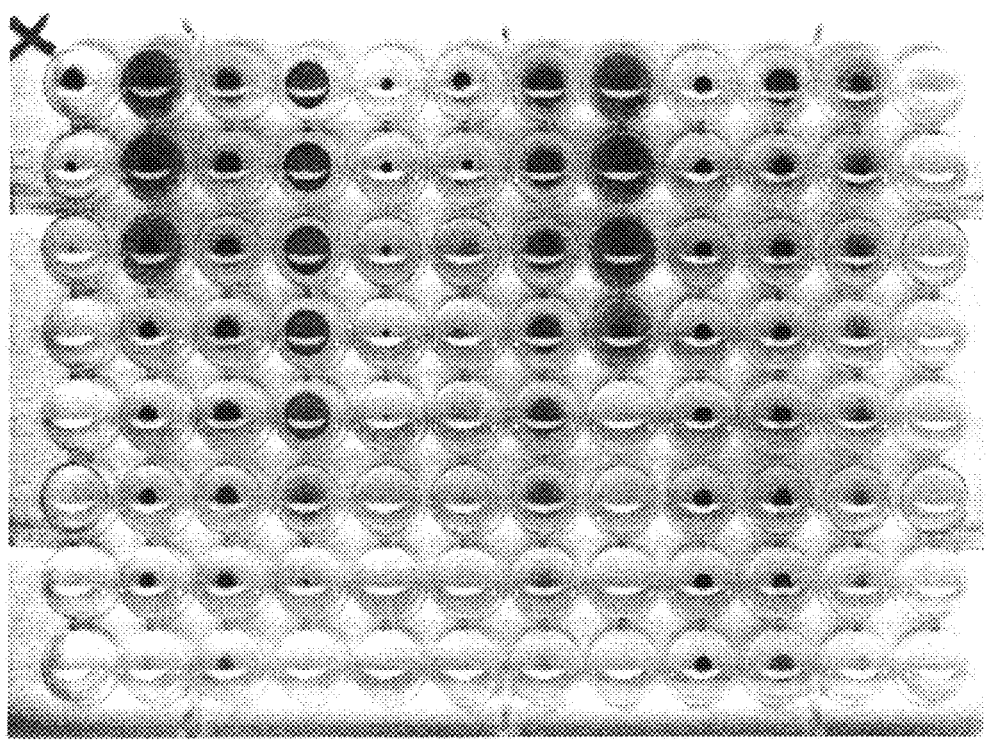
FIG. 6 shows an example of an outcome from a MARA toxicity assay as analysed with the MARA software.

FIG. 6 shows the outcome of an experimental assay with the indicator device according to the present invention. In FIG. 6 an incubated MARA plate was read by a flatbed scanner. The plate was exposed to a concentration gradient of a chemical, of which the toxicity was to be evaluated. The MARA reading software measures the size and intensity of the pellets that are result of the bacterial growth in the wells and compares the pellet in each column to that of the unaffected bacteria in the first row. The resulting toxic fingerprint was compared to toxic fingerprints of known compounds in a database, and the similarities to those values were calculated. In the example above, a very high similarity value (0.89) was obtained when compared to acryl amide. This could indicate that the unknown compound has biological effects similar to those of acryl amide.

Figure 7:
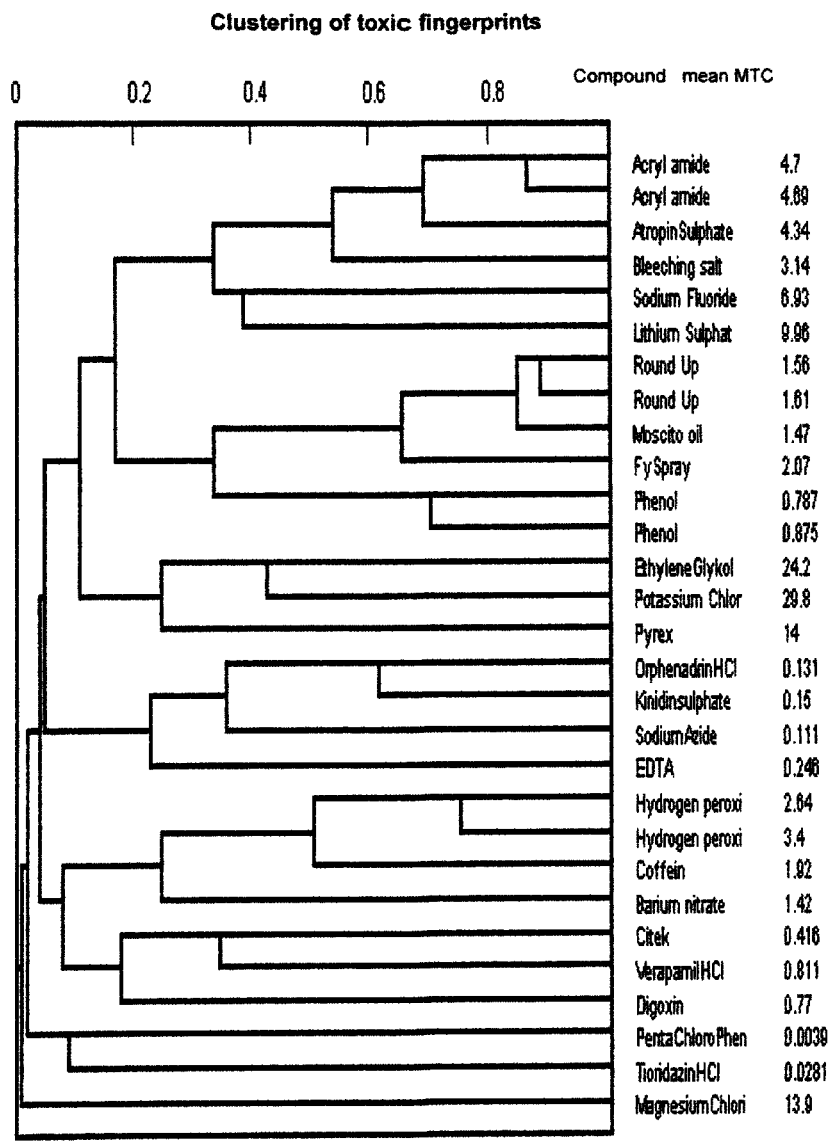
FIG. 7 shows a toxic fingerprint.

FIG. 7 shows an example on how the generation of toxic fingerprints with the indicator device and subsequent cluster analysis of data can give more information on the chemical compounds assayed than just an indication on level of toxicity would do. The figure illustrated is a dendrogram, derived from clustering of the similarity coefficients obtained from comparisons of the toxic fingerprints of different standard chemicals. The discrimination power and the reproducibility (comparisons between different assays) of the toxic fingerprints is also visualized in the dendrogram. The figure shows that the similarities between the toxic fingerprints of the same chemical compounds, even when assayed at different occasions, are higher than between different chemical compounds, thus indicating a high reproducibility of the toxic fingerprints. Although in some cases the reproducibility is below 0.8, the similarities between the toxic fingerprints of the same chemical compounds, even when assayed at different occasions, are higher than between different chemical compounds.

The dendrogram in FIG. 7 also indicate the approach for building up a database of toxic fingerprints for different compounds of known toxicity. Compounds with different toxicity levels will of course cluster differently with the database, however compounds with similar toxic levels but different biological effects should preferably also cluster different according to their toxic fingerprints. An example of this in the FIG. 7 is Round Up (a herbicide—non toxic for microorganisms according to the producer) and the simple inorganic salt Barium Nitrate, that show similar mean toxicity levels (MTC values 1.6 and 1.4 mg/l, respectively), but that cluster in different groups according to their toxic fingerprints. Other examples are Phenol (very toxic and also carcinogenic) and Digoxin (a heart medicin, originally derived from the plant Digitalis lanata), both with MTC levels of 0.8, but clustering very different. These examples show that compounds showing similar average toxicity values, but have totally different biological effects also could be separated with the MARA assay. By building a data base with toxic fingerprints of compounds of which the toxic effects have already been careful evaluated, and comparing new compounds to this database, we are able to predict some of their biological effects.

EXAMPLES

Example 1

Cultivation and Lyophilization of Micro-organism With Subsequent Stability Study The microorganism were first cultivated on nutrient agar for 24 h at 30° C. From each strain a loopfull of microorganism was suspended lyophilization media. 25 µl of the microbial suspensions were dispensed into each well in the flat-bottomed microplates, Lyophilisation of microorganism in microplates was carried out according to standard methods. After the lyophilisation, each microplate was packed in an air-tight plastic-aluminium bag together with silica gel. The plastic-aluminium bag was then sealed. The plates were stored at three different temperatures: at room temperature, at refrigerator temperature (4° C.) and at −20° C.

In order to define an appropriate lyophilization medium and storage and transportation conditions for the microplates containing lyophilized microorganism, the numbers of viable microorganism were determined directly after lyophilisation, and after one week, one month and two months of storage. Each lyophilised microbial strain was subject to 10-fold dilutions in phosphate buffer saline (PBS), and the dilutions were spread on nutrient agar plates, which were incubated at 30° C. for 24 h, whereupon the number of viable microorganisms was estimated as the number of colonies on the agar plates.

In order to assure that the lyophilised microorganisms were kept in the microplate wells even under rough conditions (such as during transportation), the following test was performed: Sterile membrane filters were placed on the top of microplates with lyophilized microorganism. The plates were kept upside down in a sealed plastic bag on a shaking table for 24 h. The filters were then placed on nutrient agar plates and incubated.

Plates with lyophilised microorganism only in every second column were used to determine the risk of contamination between wells with different strains. All wells were filled with growth medium and glucose and the plates were incubated at 30° C. If also wells containing no microorganism had been contaminated with microorganism, this would result in an indicator change in these wells.

Microbial responses to different chemicals was estimated by kinetic measurements of their growth using the Labsystem automated IEMS reader. A computer software that could monitor incubation temperatures, reading intervals, and automatically transfer OD data to a computer was developed. A growth medium containing 0.05% peptone, 0.011% bromothymol blue (BTB), 1% sodium chloride and 0.3% glucose was added to all wells. The glucose acts as a carbon source, and during growth the microorganism will break down the glucose and produce acids, that will turn the initially blue indicator to yellow. Each microplate contains 12 columns and 8 rows, and thus in each plate, 11 lyophilized microbial strains were used (one for each column, the 12th column was used as negative control). To the microplate decreasing concentrations of the chemical compound to be tested was added to rows A-G. Row H was kept as a control, to show the results of unaffected bacteria. In order to avoid drying out of the plates during the incubation, one drop of sterile mineral oil was added to each well. The plate was then incubated in the IEMS spectrophotometer and the absorbance value from each well was measured every second hour during 48 h.

The reproducibility of the assay was estimated by using different lyophilized microplates with the same set of microorganism. Growth kinetics at 30 and 22° C., as well as growth kinetics of non-lyophilized versus lyophilized cultures was compared in the same way.

A software that could present the growth curves from all wells and analyse the kinetic data was developed. IC50 (50% inhibitory concentration) values for the assayed chemicals were estimated as the lowest concentration yielding <=50% of the growth response of the unaffected micro-organism.

For the study, a simple detection method based on the kinetics of microbial growth in the presense of glucose as carbon source has been used. Another detection method that was also investigated was the reduction of triphenyl-tetrazoliumchloride, also with glucose as carbon source.

All lyophilization procedures yielded a decrease in microbial count; however, the number of survivors was still high enough to give a fast growth response. Lyophilisation was most successful with standard media and in buffer-glucose-media. The addition of polymer mixture was not suitable in this case, even though a lower concentration could be useful for better preserving the micro-organism.

The survival of the lyophilized microorganism in three lyophilization media and stored at room temperature, refrigerator and at −20° C. was assayed after one week, one month and after two months. Most of the lyophilised microorganism survived well for one week at room temperature in standard media and quite well in buffer-glucose-media. Storage at refrigerator temperature and at −20° C. kept an acceptable amount of microorganisms alive for one month in buffer-glucose-media and for at least two month in standard media.

The responses of a set of selected microbial strains to several chemicals were measured as MTC values (Microbial Toxic Concentration) values (Table 2). The responses of the different strains used normally varied, for example acrylamid yielded an MTC value of 20 to E. coli, but only 0.9 towards strain 1 with an incubation time of 16 h. Table 2 shows toxic fingerprints from some standard chemicals and mixed compounds obtained with the indicator device, and using 11 different microbial strains. Reproducibility from duplicate assays on different occasions is shown for some chemicals. The overall toxicity of the chemical compound can be described either as the mean of all 11 MTC values (shown in column 12), or as the minimum value for all 11 microbial strains used in the assay (marked with bold in the table). It is obvious from the table that no single microbial strain shows a high sensitivity to all compounds, and by selecting only one strain for an assay (as is done in most existing assays), the sensitivity for some chemical compounds will be decreased. It is also obvious from the table that by measuring the overall toxicity only, most of the information obtained from the results from individual microbial strains would be lost, and therefore the present invention suggests the use of the toxic fingerprints, i.e. that all data are used.

TABLE 2

Examples of toxic fingerprints from some standard chemicals and mixed compounds obtained with the indicator device. Reproducibility from duplicate assays on different occasions are shown in some cases

| | Toxic fingerprint: MTC value for microorganism no. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | Mean | Sd |
| Acryl amide | 0.965 | 2.440 | 4.280 | 2.100 | 5.740 | 2.480 | 3.890 | 17.700 | 13.900 | 6.620 | 8.300 | 4.700 | 1.121 |
| Acryl amide | 0.853 | 1.810 | 3.370 | 2.510 | 3.240 | 2.810 | 12.200 | 23.300 | 11.000 | 6.970 | 10.300 | 4.690 | 1.429 |
| Round Up | 1.650 | 0.642 | 0.601 | 0.883 | 1.680 | 1.410 | 2.030 | 2.700 | 3.340 | 0.545 | 0.540 | 1.560 | 0.605 |
| Round Up | 1.140 | 0.863 | 0.390 | 1.030 | 1.400 | 1.320 | 3.770 | 3.300 | 5.530 | 0.938 | 0.313 | 1.610 | 1.026 |
| Phenol | 0.588 | 0.432 | 0.138 | 0.888 | 0.589 | 0.954 | 0.760 | 1.420 | 1.270 | 0.447 | 0.800 | 0.787 | 0.476 |
| Phenol | 0.557 | 0.528 | 0.240 | 0.720 | 0.526 | 0.490 | 2.140 | 3.160 | 1.940 | 0.377 | 0.799 | 0.875 | 1.073 |
| Hydrogen peroxide | 1.110 | 1.460 | 0.492 | 9.650 | 10.600 | 0.184 | 1.540 | 15.100 | 1.260 | 0.082 | 0.852 | 2.640 | 2.001 |
| Hydrogen peroxide | 1.140 | 4.730 | 1.670 | 10.500 | 15.900 | 0.628 | 4.860 | 17.300 | 0.776 | 0.411 | 0.837 | 3.400 | 1.861 |
| Ethylene Glycol | 14.200 | 15.900 | 17.900 | 24.400 | 16.200 | 14.400 | 20.300 | 77.300 | 26.100 | 15.600 | 22.000 | 24.200 | 0.749 |
| Ethylene Glycol | 17.000 | 17.900 | 17.400 | 30.900 | 14.400 | 27.100 | 71.600 | 90.200 | 19.300 | 7.950 | 29.300 | 32.600 | 0.792 |
| Sodium Fluoride | 3.290 | 2.660 | 6.900 | 6.040 | 9.500 | 4.090 | 6.450 | 11.400 | 22.700 | 5.650 | 4.970 | 6.930 | 0.812 |
| Sodium Fluoride | 2.220 | 2.930 | 17.300 | 6.560 | 15.000 | 13.900 | 7.890 | 14.600 | 20.100 | 4.130 | 10.300 | 9.170 | 0.669 |
| Lithium Sulphate | 3.700 | 6.300 | 12.200 | 4.590 | 14.500 | 10.600 | 10.000 | 41.800 | 23.400 | 2.650 | 22.400 | 9.960 | 1.165 |
| Lithium Sulphate | 4.780 | 7.170 | 12.700 | 7.950 | 10.000 | 8.490 | 29.800 | 25.400 | 17.500 | 3.570 | 15.300 | 12.700 | 0.662 |
| Penta Chloro Phenol | 0.006 | 0.001 | 0.000 | 0.009 | 0.007 | 0.003 | 0.005 | 0.005 | 0.004 | 0.005 | 0.001 | 0.004 | 0.686 |
| Penta Chloro Phenol | 0.004 | 0.001 | 0.001 | 0.010 | 0.004 | 0.006 | 0.007 | 0.006 | 0.003 | 0.011 | 0.001 | 0.005 | 0.649 |
| Orphenadrin HCl | 0.027 | 0.053 | 0.130 | 0.222 | 0.216 | 0.082 | 0.133 | 0.173 | 0.177 | 0.034 | 0.134 | 0.131 | 0.528 |
| Orphenadrin HCl | 0.075 | 0.082 | 0.127 | 0.203 | 0.131 | 0.118 | 0.147 | 0.129 | 0.298 | 0.050 | 0.172 | 0.146 | 0.467 |
| Kinidin sulphate | 0.108 | 0.053 | 0.113 | 0.243 | 0.142 | 0.099 | 0.138 | 0.287 | 0.254 | 0.091 | 0.088 | 0.150 | 0.520 |
| Kinidin sulphate | 0.102 | 0.076 | 0.104 | 0.233 | 0.055 | 0.141 | 0.275 | 0.135 | 0.329 | 0.072 | 0.085 | 0.145 | 0.632 |
| Coffein | 0.529 | 1.080 | 2.630 | 3.780 | 3.550 | 1.300 | 1.510 | 3.500 | 2.140 | 0.785 | 2.310 | 1.920 | 0.604 |
| Caffeine | 0.731 | 1.010 | 4.000 | 2.640 | 0.973 | 2.190 | 2.930 | 3.430 | 5.030 | 0.790 | 6.060 | 2.250 | 0.803 |
| Atropin Sulphate | 0.535 | 2.110 | 3.890 | 4.670 | 3.890 | 3.490 | 3.290 | 6.710 | 5.970 | 2.610 | 5.820 | 4.340 | 0.420 |
| Atropin Sulphate | 1.630 | 1.660 | 2.670 | 4.570 | 1.920 | 4.730 | 6.460 | 8.060 | 7.960 | 1.830 | 6.210 | 3.670 | 0.693 |
| Bleaching salt | 1.150 | 1.120 | 0.749 | 1.740 | 3.890 | 1.530 | 1.550 | 10.700 | 2.130 | 1.480 | 0.877 | 2.110 | 1.359 |
| Bleaching salt | 1.420 | 1.290 | 1.870 | 1.540 | 4.420 | 3.770 | 1.230 | 6.320 | 6.000 | 2.680 | 5.390 | 3.140 | 0.634 |
| Citek | 0.280 | 0.404 | 0.094 | 0.810 | 0.777 | 0.391 | 0.597 | 0.230 | 0.270 | 0.351 | 0.052 | 0.416 | 0.601 |
| Citek | 0.318 | 0.225 | 0.226 | 0.863 | 0.646 | 0.567 | 1.080 | 0.552 | 0.269 | 0.483 | 0.076 | 0.562 | 0.537 |
| Digoxin | 1.040 | 0.937 | 0.481 | 0.942 | 0.927 | 0.531 | 0.921 | 0.310 | 0.201 | 2.510 | 0.104 | 0.770 | 0.852 |
| Barium nitrate | 2.520 | 0.205 | 0.908 | 5.620 | 1.090 | 0.713 | 1.110 | 1.360 | 1.490 | 0.453 | 0.466 | 1.420 | 1.071 |
| Tioridazin HCl | 0.016 | 0.017 | 0.011 | 0.067 | 0.029 | 0.027 | 0.042 | 0.006 | 0.009 | 0.014 | 0.006 | 0.028 | 0.658 |
| Verapamil HCl | 0.326 | 0.247 | 0.128 | 3.100 | 0.591 | 1.090 | 2.950 | 0.360 | 0.510 | 0.877 | 0.371 | 0.811 | 1.306 |
| Potassium Chloride | 28.200 | 29.400 | 10.600 | 17.000 | 20.100 | 27.100 | 67.300 | 62.300 | 65.400 | 16.000 | 31.300 | 29.800 | 0.701 |
| EDTA | 0.029 | 0.029 | 0.034 | 0.189 | 0.137 | 0.447 | 1.240 | 1.840 | 1.090 | 0.679 | 0.791 | 0.246 | 2.442 |
| Magnesium Chloride | 28.800 | 9.660 | 7.420 | 7.500 | 14.800 | 13.500 | 12.100 | 24.100 | 8.830 | 22.700 | 4.580 | 13.900 | 0.567 |
| Sodium Azide | 0.025 | 0.045 | 0.056 | 0.088 | 0.054 | 0.082 | 0.126 | 0.592 | 2.000 | 0.106 | 0.146 | 0.111 | 5.268 |
| Mosquito oil | 0.690 | 0.641 | 0.110 | 1.070 | 1.800 | 1.600 | 1.610 | 4.180 | 5.720 | 0.747 | 0.209 | 1.470 | 1.189 |
| Pyrex | 5.390 | 6.710 | 0.015 | 10.300 | 5.680 | 5.220 | 19.300 | 14.000 | 18.400 | 16.300 | 14.800 | 14.000 | 0.455 |
| FySpray | 0.419 | 0.291 | 0.155 | 1.350 | 0.241 | 1.950 | 4.670 | 105.000 | 50.000 | 2.360 | 0.161 | 2.070 | 16.048 |

The micro-organisms used were:
1-4 JG1-JG4 (strains of marine origin)
 5 β-proteobacterium A22 (Kalmar 200)
 6 *Aeromonas hydriphila* HG3 (RV 5.1)
 8 *E. coli* MZ 480
 9 ObanF
10 *Saccaromyces ceriviciae* (bakers yeast)
11 *Staphylococcus epidermidis* (Karin12)

The response of our strains to some chemical compounds was also compared with some established ecotoxicological assays (Table 3).

Table 3 shows comparisons between the MARA and some established toxicity assays, when only the overall toxicity is measured with the MARA. Concentrations are given in mg/ml. As can be seen in the table, the sensitivity of MARA is well within the range of the established tests. Compared to Microtox, the mean MTC values in MARA show similar responses in 7 of the 14 evaluated compounds, show more sensitive responses to 3 compounds, and lower responses to 4 compounds. Using minimum MTC values in MARA, the sensitivity increases and is for all compounds but two higher than or equal to that of Microtox. This indicates that MARA is a useful toxicity test, also when used in the conventional way, i.e. without comparisons to a database. The MARA results are given as minimum MTC-values ($MTC_{min}$) (MTC value of the bacterial strain showing the highest sensitivity to the actual compound) and as mean MTC-values ($MTC_{mean}$) for the 11 microbial strains used; results from others assays are given as $IC_{50}$-values. However, MARA does not just give a simple concentration value (shown above is the mean or min MTC-value) but a vector of concentrations giving the toxic fingerprint of the tested chemical compounds (FIG. 6). This can not be obtained from any of the other tests.

ganism and concentration of the pollution, at certain time-intervals. Although some microorganisms did not seem to survive very well, the number of microbial strains that could be used for the assay is so large that there will be no difficulties to determine sets of appropriate strains One problem might be caused by the escape of microorganism from the bottom of the wells during the lyophilization procedure, and subsequent contamination to other wells. However, since this only occurred in 1% of all cases we assayed, this seems to be a minor problem that can easily be

TABLE 3

Comparisons between MARA and some established toxicity assays

| | | Inhibitory concentrations by method | | | | |
|---|---|---|---|---|---|---|
| MEIC nr | Compound | Daphnia | E. coli | Microtox | MARA $MTC_{min}$ | MARA $MTC_{mean}$ |
| 6 | Digoxin | 0.192 | | 1.129 | 0.104 | 0.770 |
| 7 | Ethylene glycol | 74.625 | 270.945 | 167.064 | 11.775 | 28.400 |
| 12 | Phenol | 0.007 | 2.258 | 0.133 | 0.412 | 0.831 |
| 14 | Sodium fluoride | 0.636 | 10.547 | 9.843 | 4.890 | 8.050 |
| 20 | Lithium sulfate | 0.033 | 67.764 | 25.763 | 3.11 | 11.330 |
| 29 | Thioridazine HCl | 0.005 | 0.059 | 0.008 | 0.006 | 0.028 |
| 37 | Barium nitrate | 0.208 | | 29.318 | 0.453 | 1.420 |
| 39 | Pentachlorophenol | 0.001 | 0.010 | 0.001 | 0.001 | 0.005 |
| 40 | Verapamil HCl | 0.055 | 0.834 | 0.438 | 0.360 | 0.811 |
| 42 | Orphenadrine HCl | 0.011 | 0.701 | 0.119 | 0.100 | 0.139 |
| 43 | Quinidine sulfate | 0.062 | 1.009 | 0.092 | 0.087 | 0.148 |
| 48 | Caffeine | 0.158 | 15.426 | 2.129 | 0.788 | 2.085 |
| 49 | Atropine sulfate | 0.347 | 56.294 | 3.094 | 2.220 | 4.005 |

The sensitivity of our indicator device is thus well within the range of the established tests. Compared to Microtox, the mean MTC values in MARA show similar responses in 7 of the 14 evaluated compounds, show more sensitive responses to 3 compounds, and lower responses to 4 compounds. Using minimum MTC values in MARA, the sensitivity increases and is for all compounds but two higher than or equal to that of Microtox. This indicates that MARA (i.e the method according to the present invention) is a useful toxicity test.

Examples of the reproducibility of the toxic fingerprints are also shown in table 2. The plates were assayed at different occasions, with different preparations of the chemicals. The method used when establishing growth kinetics of microorganism using glucose as carbon source and a pH indicator—has proven useful, however, it would limit the microbial strains that may be used to those that can utilize glucose with the production of acids. Using triphenyl-tetrazoliumchloride instead of a pH indicator somewhat decreased the sensitivity of the assay. It also did not increase the rate of response, but could have other advantages by allowing the use also of non-fermentative microorganisms.

Several other assays may be used, e.g.: LIVE/DEAD Baclight Bacterial Viability Kit from Molecular Probes, Inc. The kit provides two different nucleic acid stains, SYTO 9 and propidium iodide, to distinguish between live and dead bacteria. Live bacteria are labelled green by the membrane-permeable SYTO 9 stain and dead bacteria are labelled red by the membrane-impermeable propidium iodide. Staining is done in ten minutes and the measurement is then performed with a fluorimeter at the two wavelengths. This method would allow a rapid detection of the toxicological response to complex polluting agents. A pseudo kinetic measurement could be done by staining the wells, containing the same microorovercome by the use of e.g. more careful lyophilization procedures, or the use of some kind of semi-permeable covers for the plates.

Even if the microorganism assayed in the study showed better survival rates at freezer temperatures than at room temperature, most of them survived also well during storage at room temperature for shorter periods of time. This means that a ready product could be easily transported by normal mail. However, storage for prolonged times should preferably be done at −20° C. The plates also showed a good stability during shaking, using all three of the lyophilization media we tested, which also indicates that they can easily be transported.

One requirement of the assay is that it should give a varied response from different organisms to toxic chemicals. This requirement can be met by selecting the appropriate microbial strains. An assay according to the present invention using only 11 microbial strains showed a quite broad interval of tolerances; however, it was not far as high as the interval obtained with the various organisms.

Our data indicate a reasonable reproducibility from duplicate assays, however when assays are performed at different temperatures variations may occur. Thus, it is important that cells are treated the same way if different assays are to be compared with each other.

In the present study, the inhibitory effect on the studied microorganism was calculated as simple IC50 values (50% Inhibitory Concentration) or as MTC values (this is a variant of the commonly used LOEL values—lowest effective level). These methods have proven useful in many other investigation, where the response is given as only a +/− value (e.g. reaction/no reaction). However, quantitative growth measurements like used here or kinetic measurements could give much more information than only a + or − value.

Example 2

Collection of Micro-organism, Production of Media and Growth Test

The strains were collected from the environment. The isolates may be characterized by Gram staining, catalase and oxidase test, growth on different agar media, and their ability to give measurable growth responses with the indicators BromoThymol Blue (BTB, an acid-base indicator) and 2,3,5-triphenyl-terazolium chloride (TZR, a redox indicator).

A large subset of the strains showed good growth response in the presence of TZR, whereas fewer reacted well with BTB indicator.

The following protocol was used
1. The strains that were going to be lyophilised were taken from the freezer and grown on nutrient agar (DIFCO) plates over night in 28° C.
2. Colonies were taken from the agar plates and grown in 25 ml tubes containing 3 ml nutrient broth (DIFCO), 28° C. over night on a shaking table
3. The broth was centrifuged (15 min, 3000 rpm) and the supernatant was removed All strains in the present strain collection grew well on nutrient agar/broth.

In order to verify that the microorganisms survive lyophilisation, their survival was studied using different cryoprotectants such as polyvinylpyrrolidine and glycerol.

Over 80 strains that can be lyophilised, and that can yield measurable growth responses have been tested.

Lyophilisation media: A lyophilisation medium that is suitable for most assayed microorganism was developed. The composition was as follows:

2% dextran
7,5% glucose
0,3 M phosphate buffer

Nutrient broth is added to support growth of most microorganism. Glucose is a growth promoting chemical, and it also improves the attachment of the lyophilised micro-organism to the surface of the microplates. Dextran is a carbohydrate polymer that acts as a protective agent for the microbial cells during the lyophilisation, and also improves attachment to the microplates and the compactness of the pellets.

Survival time and reproducibility: Strains may preferably survive at least one year at −20° C. and at least one week at room temperature. Tests so far has revealed that the survival time of the lyophilized micro-organism in the microplates has been at least 3 months in −20° C. The plates were being kept at different storage temperatures and tested continuously according to the below scheme given in table 4.

phosphate buffert (see above). In order to obtain good microbial growth, only nitrogen source, trace elements and indicator were further required for the assay, according to the present invention. Normal nutrient broth (NB) has been used (DIFCO), which has worked well.

Recipe to make up 1 liter of assay medium:
0,1 g tetrazolium salt*
10 g NaCl
8 g nutrient broth

* Tetrazolium red (2,3,5-triphenyltetrazoliumchloride) precipitates when being autoclaved with nutrient broth and the same thing may happen with other tetrazolium salts and with resazurin. Either NB and the indicator may preferably be autoclaved as separate solutions or the solution can be sterile filtered.

The working parameters of the method (assay) according to the present invention regarding incubation may be for the plates over night at 28° C.

Assessment of growth and replication type stress assays using both colorimetric and fluorescent markers for growth and replication may be done (turbidity, increased fluorescence after staining with propidium, nalidixic acid method). This may include kinetic growth.

Evaluate may be done of the response of the assay both to simple, model compounds and to ecologically relevant, complex pollutants. Test data was obtained to simple and complex chemical compounds and strain collection suitable for use in demonstration project was made.

Simple model compounds from the MEIC (Multicentre Evaluation of In vitro Cytotoxicity) list was screened to provide comparative data on the performance of the assay against existing toxicity assays. 40 of the chemicals from the "First 50" reference chemicals of the MEIC project were tested.

Defining the response of the assay to therapeutics used in aquaculture (5 compounds) drawn from antibiotic formulations and anti-lice treatments was done, when used in Scotland by salmon farms. Defining the response of the assay to complex mixtures (sedimentation from fish farms, drill cuttings from oil production) was also done. Efficiency of assay in response to complex mixtures was measured.

An appropriate and responsive array of microbial strains from previous collection, may be used obtained from culture collections of microbial strains most suitable for the assay.

Comparison of the results obtained from the assay with those obtained from existing methods of impact assessment using real samples was done. To investigate the hypothesis that patterns of response from complex chemical compounds that match patterns induced by simple model compounds indicate a similar level of risk. Evaluation of assay was done in response to "real life" ecotox assessments. The assay was

TABLE 4

| Stability test procedure | | | | | | |
|---|---|---|---|---|---|---|
| Room temperature | 2 days | 4 days | 7 days | 9 days | 11 days | 13 days |
| +8° C. | 2 weeks | 4 weeks | 6 weeks | 8 weeks | 10 weeks | 12 weeks |
| −20° C. | 3 months | 6 months | 9 months | 12 months | | |

As model substances (stress indicators) in the assay a short list of well-defined chemicals was used. These included Phenol, acrylamide, ethylene glycol, isopropylamino-glyphosphate ("Roundup"), glycerol, DMSO and formaldehyde.

Defining a cultivation medium that allows growth of all microbial strains in the assay, and that does not interfere with the detection method was done. The microorganism were lyophilized in a medium containing dextran, glucose, and tested with marine samples being tested for ecotoxicity as part of SEPA's regulatory role. The results was compared with those obtained by other standard ecotox assays being used at the same time (notably Microtox above)

Comparison was done with community analysis—field testing of assay in conjunction with community and limited chemical analyses at the same locations along gradients of organic enrichments (fish farms and sewage disposal sites).

Effects of the environmental factors were analysed using multivariate statistical methods (eg Canonical correspondence analyses).

Example 3

The present example (results of which may be seen in FIG. 6) was performed according to the method of the present invention. An indicator device according to the present invention was also used. The pattern that was read and can be seen in FIG. 6 was compared in a computer to standard patterns whereby a correlation was obtained.

11 microbial strains in column 1-11 were used and column 12 served as control.

Unknown compound was added at a concentration of 6.4 mg/ml to all wells in row H, 3.2 mg/l to row G etc.

The parameters in the microplate were as follows: Min. conc.=0.1, Max. conc.=6.4, Dilution steps=2

Table 5 shows the relative growth amounts for the bacteria obtained after the incubation.

TABLE 5

Relative growth for bacteria in example 3.
Unknown compound Min. konc = 0.1% Max. konc = 6.4% Dilution steps = 2

| Konc. | Bacterium | | | | | | | | | | | NEG | Mean |
|---|---|---|---|---|---|---|---|---|---|---|---|---|---|
| | 1 | 2 | 3 | 4 | 5 | 6 | 7 | 8 | 9 | 10 | 11 | | |
| 0 | 1360 | 1526 | 1374 | 891 | 523 | 1123 | 1061 | 1054 | 1218 | 1245 | 915 | 0 | 1024 |
| 0.1 | 557 | 1534 | 1425 | 1020 | 581 | 847 | 1099 | 1065 | 1436 | 1183 | 662 | 0 | 951 |
| 0.2 | 49 | 1515 | 1354 | 1018 | 543 | 334 | 1074 | 1166 | 1317 | 1135 | 570 | 0 | 840 |
| 0.4 | 0 | 1159 | 1329 | 915 | 293 | 231 | 791 | 981 | 1170 | 933 | 314 | 0 | 676 |
| 0.8 | 0 | 1144 | 1367 | 812 | 53 | 85 | 684 | 14 | 1246 | 957 | 381 | 0 | 562 |
| 1.6 | 0 | 899 | 1220 | 568 | 0 | 95 | 600 | 0 | 1342 | 836 | 305 | 0 | 489 |
| 3.2 | 0 | 857 | 1041 | 337 | 0 | 0 | 302 | 0 | 1307 | 768 | 128 | 0 | 395 |
| 6.4 | 0 | 28 | 390 | 0 | 0 | 0 | 61 | 0 | 902 | 387 | 0 | 0 | 147 |
| Toxic fingerprint | 0.07 | 1.27 | 2.76 | 1.41 | 0.31 | 0.13 | 0.95 | 0.41 | 4.49 | 1.58 | 0.30 | — | 0.78 |

The results were as follows:

| Microbial Toxic Concentration (MTC) | Mean 0.78% | Min 0.07% |
|---|---|---|

| Highest similarity of toxic fingerprint to known compounds in data base | |
|---|---|
| Acryl amid | 0.89 |
| Phenol | 0.60 |
| Hydrogen peroxide | 0.30 |
| Roundup | 0.25 |
| Ethylene glycol | 0.10 |

The image in FIG. 6. shows an incubated MARA plate that was read by a flatbed scanner. The plate was exposed to a concentration gradient of a chemical compound, of which the toxicity was to be evaluated. The MARA reading software processes the measured size and intensity of the pellets that are result of the bacterial growth in the wells and compares the pellet in each column to that of the unaffected bacteria in the first row. The resulting toxic fingerprint was compared to toxic fingerprints of known compounds in a database, and the similarities to those values were calculated. In the example above, a very high similarity value (0.89) was obtained when compared to acryl amide. This could indicate that the unknown compound has biological effects similar to those of acryl amide. FIG. 6 shows the relative growth amounts for the micro-organism obtained after the incubation, and the results as toxic fingerprint, Mean and Minimum MTC value, and a printout of the similarities to the compounds in the preliminary data base that were most similar to the unknown compound. It appeared that the toxic effects were most similar to those produced by acryl amide when comparing with known compounds in database. Compare also the dendrogram in FIG. 7.

It should be understood that modifications can be made to the embodiments disclosed herein. Therefore the above description should not be construed as limiting, but merely as exemplification of preferred embodiments. Those skilled in the art will envision other modifications within the scope of the claims appended hereto.

The invention claimed is:

1. A method for determining toxicity of an environmental or chemical sample containing potentially toxic chemical compounds, comprising:
(i) providing an array of at least three different microorganisms in a multi-well plate, wherein the at least three different microorganisms freeze dried are each separately present in at least four wells of a set of wells;
(ii) adding growth media and an indicator that changes color due to the growth of the microorganism to the microorganisms in the multi-well plate and exposing each of the at least three different microorganisms in the set of wells to a known concentration gradient of the sample, while leaving a well of the set of wells unexposed to the sample;
(iii) incubating the array of microorganisms;
(iv) measuring growth of each of the at least three different microorganisms in each well;
(v) within each set of wells, comparing the measured growth of the microorganism in each well exposed to the sample to the measured growth of the microorganism in the well unexposed to the sample;
(vi) calculating a toxic concentration (TC) value for each microorganism and assembling the calculated TC values into a toxic fingerprint of the sample, wherein the toxic fingerprint comprises the TC value of each microorganism;
(vii) comparing the toxic fingerprint of the sample to a reference toxic fingerprint for reference chemicals having known toxicity, the reference toxic fingerprint having been generated from a same said at least three microorganisms;
(viii) calculating a correlation coefficient between the toxic fingerprint of the sample and each of the reference toxic fingerprints; and (ix) determining the toxicity of the sample based on the correlation coefficient having a highest value in step (viii).

2. The method according to claim 1, wherein at least eleven different microorganisms are present in the array.

3. The method according to claim 1, wherein the indicator is a redox indicator.

4. The method according to claim 1, wherein the indicator is bromothymol blue or a tetrazolium salt.

5. The method according to claim 1, wherein the chemical sample comprises a plurality of chemical compounds.

6. The method according to claim 1, wherein the environmental sample is a sedimentation sample.

7. The method according to claim 1, wherein the environmental sample is a marine sample.

8. The method according to claim 1, wherein the environmental sample is selected from the group consisting of: sedimentation sample from a fish farm, sedimentation sample from a sewage disposal site, and drill cutting from an oil production site.

9. The method according to claim 1, wherein the at least three different microorganisms are selected from the group consisting of JG1, JG2, JG3, JG4, β-*proteobacteria, Aeromonas hydrophila, Escherichia coli, ObanF, Saccaromyces ceriviciae* and *Staphylococcus epidermidis*.

10. The method according to claim 1, wherein the TC value is calculated as a microbial toxic concentration (MTC) value or a half maximal inhibitory concentration (IC50) value.

\* \* \* \* \*